United States Patent [19]
Pappas

[11] Patent Number: 5,348,235
[45] Date of Patent: Sep. 20, 1994

[54] MEDICAL WASTE DISPOSAL SYSTEM

[76] Inventor: Charles A. Pappas, 105 Brigham St., Marlboro, Mass. 01752

[21] Appl. No.: 908,246

[22] Filed: Jul. 6, 1992

[51] Int. Cl.$^5$ .............................................. B02C 23/40
[52] U.S. Cl. ........................................ 241/41; 241/65; 241/100; 241/101.2; 241/606; 422/21; 422/299
[58] Field of Search ................. 241/41, 60, 62, 65, 241/100, 101.2, 606; 422/21, 23, 292, 298, 299

[56] References Cited

U.S. PATENT DOCUMENTS

| | | | |
|---|---|---|---|
| 2,708,074 | 5/1955 | Hoskins | 241/606 X |
| 2,731,208 | 1/1956 | Dodd | 241/606 X |
| 3,589,276 | 6/1971 | Swallert | 241/99 X |
| 4,050,907 | 9/1977 | Brimhall | 241/DIG. 38 X |
| 4,618,103 | 10/1986 | Wilson et al. | 241/606 X |
| 4,619,409 | 10/1986 | Harper et al. | 241/606 X |
| 4,860,958 | 8/1989 | Yerman | 241/99 X |
| 4,971,261 | 11/1990 | Solomons | 241/100 X |
| 4,975,246 | 12/1990 | Charm | 422/21 |
| 4,979,683 | 12/1990 | Busdeker | 241/101.2 X |
| 4,992,217 | 2/1991 | Spinello | 252/628 X |
| 5,003,143 | 3/1991 | Marks et al. | 34/1 P X |
| 5,025,994 | 6/1991 | Maitlen et al. | 241/100 X |
| 5,089,228 | 2/1992 | Meijer | 241/606 X |
| 5,124,125 | 6/1992 | Brent | 422/21 |
| 5,130,092 | 7/1992 | Liu | 241/16 X |

FOREIGN PATENT DOCUMENTS

| | | | |
|---|---|---|---|
| 54823 | 1/1982 | European Pat. Off. | 241/DIG. 38 |
| 3505571 | 8/1986 | Fed. Rep. of Germany | 422/21 |
| 3710156 | 10/1988 | Fed. Rep. of Germany | 422/21 |
| 2908086 | 9/1990 | Fed. Rep. of Germany | 422/21 |
| 8000413 | 3/1980 | PCT Int'l Appl. | 422/21 |
| 8602842 | 5/1986 | PCT Int'l Appl. | 422/21 |
| 1502093 | 8/1989 | U.S.S.R. | 241/DIG. 38 |
| 2238535 | 6/1991 | United Kingdom | 422/22 |

*Primary Examiner*—Mark Rosenbaum
*Assistant Examiner*—Frances Chin
*Attorney, Agent, or Firm*—M. K. Silverman

[57] ABSTRACT

A medical waste disposal system includes an assembly for superheating a quantity of untreated medical waste which is partially saturated with water to an internal temperature of at least 275 degrees Fahrenheit for at least thirty minutes. After such superheating the vessel is rotated to cool the same to under 100 degrees Fahrenheit after which the contents are deposited into a matrix of grinding elements having surfaces of different grinding dimensions and capabilities such that the output thereof is unrecognizable as medical waste. Such output is then deposited into a microwave assembly to further disinfect and decontaminate the medical waste. After such treatment the output of the system may be treated in the same fashion as conventional household refuse.

8 Claims, 5 Drawing Sheets

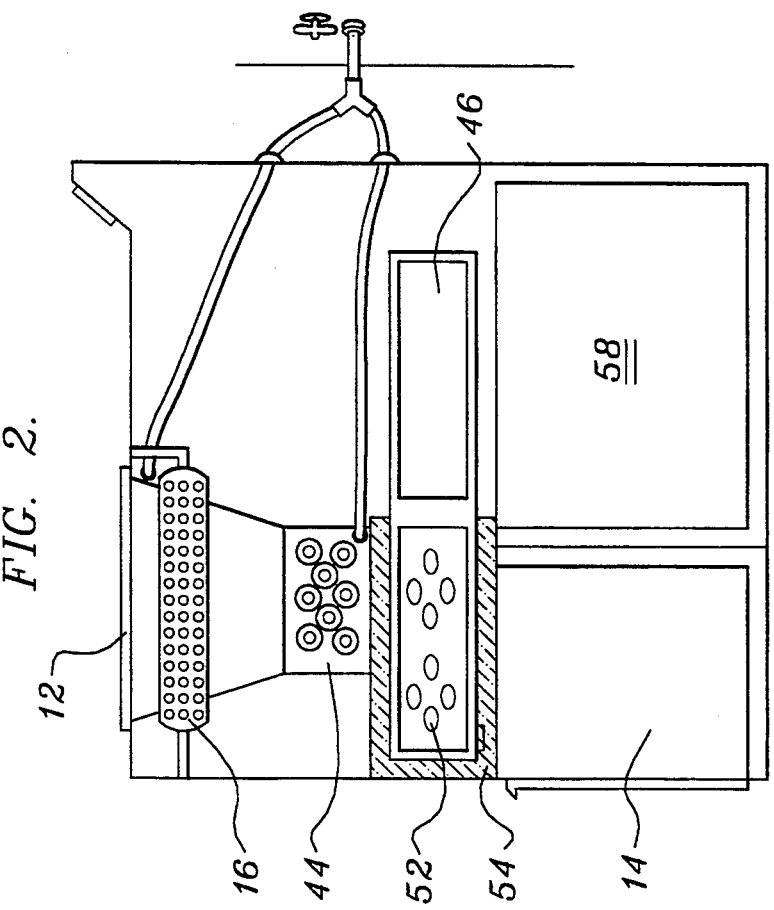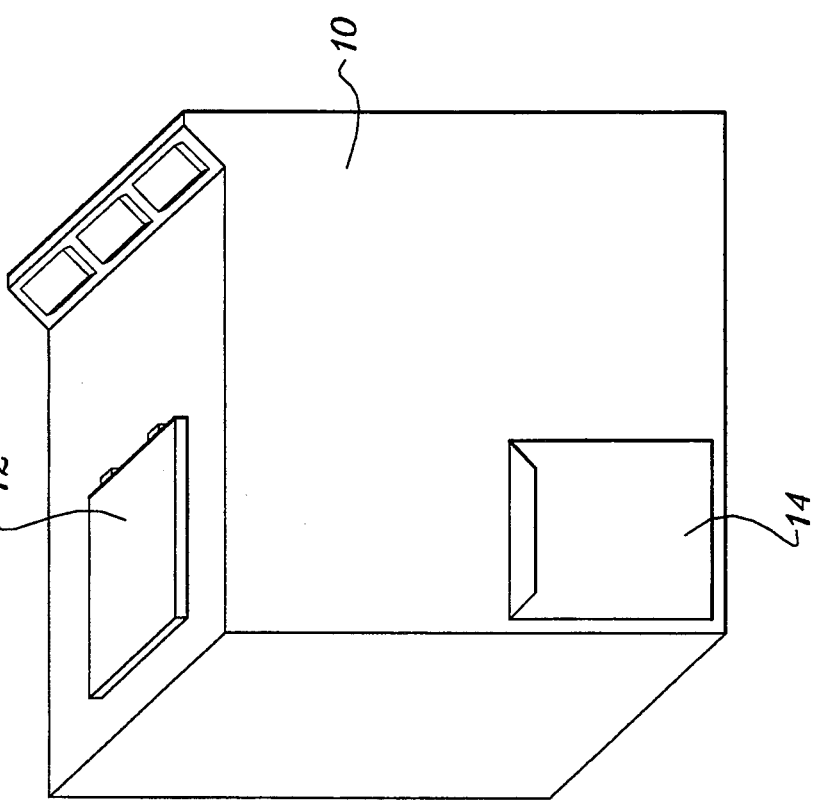

MEDICAL WASTE DISPOSAL SYSTEM

BACKGROUND OF THE INVENTION

At present, most of the more that 600,000 tons of regulated biomedical waste generated by hospitals, laboratories, clinics and medical offices in the United States are disposed of through means of off-site incineration. Such incineration, whether on-site or off-site gives rise to problems concerning compliance with the Federal Clean Air Standards Act which, as a result, have often raised capital and operating costs associated therewith to prohibitive levels.

Accordingly, some effort has been directed toward the creation of industrial sized autoclaving. However, this approach has been questioned because it cannot be assured that steam penetration will occur throughout an entire load of medical waste, given the variables of packaging and fluid volumes which may exist within any particular batch of medical waste. Further, autoclaving does not render the medical waste unrecognizable or reduce its volume. Thusly, it is unsuitable for disposal in already overcrowded landfills.

Most importantly, the storing costs and liability have caused increasingly more health care institutions to turn away from having their waste hauled to off-site treatment. However, the problem of satisfactory means of on-site treatment, by whatever means, still exists.

Prior art approaches to medical waste fragmentation and disposal, other than the approaches of autoclaving and incineration include efforts at encapsulating the contaminated waste, typically in a thermoplastic compound. Such efforts are taught in U.S. Pat. No. 4,979,683 to Busdeker, entitled Portable Small Scale Medical Waste Treatment Machine and U.S. Pat. No. 4,992,217 (1991) to Spinello, entitled Apparatus and Method For Sterilizing, Destroying And Encapsulating Medical Implement Wastes.

There is further known in the art, a number of special purpose medical waste grinders having potential value in smaller or portable type disposal systems. Such grinding approaches are shown in U.S. Pat. No. 4,971,261 (1990) to Solomons, entitled Medical Waste Fragmentation and Disposal System, and U.S. Pat. No. 5,025,994 (1991) to Maitlen, et al, entitled Medical Waste Grinder.

The use of microwaves in the disinfecting of medical waste, which comprises one aspect of the present system, is shown, with reference to the treatment of sludge in U.S. Pat. No. 5,003,143 (1991), entitled Microwave Sludge Drying Apparatus and Method. Further, the use of microwaves in a medical disinfectant system for the treatment of medical waste exists in a system commercially available from ABB Sanitec, Inc., Division of Asea Brown Boveri, known as the ABB Sanitec Microwave Disinfection System. The Sanitec system has been used in Europe since 1984 and in the United States since 1990. The Sanitec system employs two basic steps—the first that of shredding the medical waste and the second that of steam-treating the ground waste while exposing the same to microwaves.

The Sanitec system suffers from a number of problems that have limited its use in the United States. One of these is that many states do not permit infectious waste to be ground prior to treatment because such grinding creates an additional risk of exposing hospital workers to infection. It is asserted by many state regulators that when medical material containing infectious agents are manipulated and disrupted, such waste, particularly waste containing aerosols, containing microorganism are released, people can become infected through the mouth, nose and eyes as well as transdermally. A second difficulty with the Sanitec system is that its normal operating temperature, in the microwave portion thereof, is that of 203 degrees Fahrenheit. This specialists in the applicable field (which is known as epidemiology), have asserted is inadequate to confidently kill the test organism *Bacillus strarochermophilus*. Accordingly, the prior art of medical waste disposal and disinfection systems which employ microwaves have suffered from problems at the input stage regarding the possible release of infectious agents during the grinding step and, as well, at the output thereof because of inadequate temperature.

The instant invention addresses the above shortcomings of microwave and other prior art approaches of to medical waste disposal. In so doing there is provided a system concept applicable to various sized system including one that can easily be used within most doctors offices and, one that can be used on-site at a hospital and, finally, an industrial sized system which can be used off-site at designated medical waste disposal locations.

SUMMARY OF THE INVENTION

The inventive medical waste disposal system comprises a fluid-tight drum for superheating a quantity of untreated medical waste that is at least partially water-saturated, to at least 275 degrees Fahrenheit for at least thirty minutes, said fluid-tight means having a selectably openable and closeable input. The drum will deposit its contents into a matrix of grinding elements having surfaces of respectively different grinding dimensions, said grinding dimensions proportioned to dimensions of the medical waste to be processed. The system further includes means for exposing to microwave energies, the ground waste output of said matrix of grinding elements, said microwave exposing means including water-misting means directed to the medical waste material prior to microwaving to assure an uniform microwave penetration which will heat the ground waste to a temperature of about 270 degrees (the normal operating temperature of an autoclave). After microwaving, the treated waste is deposited into a disposal chute into which may, optionally, be incorporated compaction means and/or encapsulation means. All openings of the system to the external environment are covered by hepa-filters to catch any potentially harmful airborne pathogens that may not have been neutralized by the system.

It is an object of the present invention to provide a medical waste disposal system, the output thereof may be treated as conventional solid garbage or waste.

It is another object of the invention to provide a medical waste disposal system which can be made in small and portable units suitable for use within a doctor's office and upon hospital grounds.

It is a further object of the present invention to provide a medical waste disposal system which does not in the normal operation thereof create any emissions into the atmosphere.

It is a yet further object of the invention to provide a medical waste disposal system having a sufficiently high operating temperature to kill any known test bacteria or organism.

It is another object to provide a waste disposal system having redundancy of disinfecting capability.

It is yet another object to provide a medical waste disposal system in which one level of disinfection occurs prior to mechanical manipulation of the medical waste.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 1 is a perspective view of a first embodiment of the present invention.

FIG. 2 is a side schematic view of the embodiment of FIG. 1.

FIG. 4A is a radial cross-sectional view taken along Line 4—4 of FIG. 2.

DETAILED DESCRIPTION OF THE INVENTION

With reference to FIG. 1 there is shown a housing 10 of a first embodiment of the invention having, therein, an input opening 12 and a chute-like output opening 14.

With reference to FIG. 2 a number of the interior mechanical components are shown in schematic view. More particularly, at the bottom of the chute of opening 12 is shown a vessel which is in the nature of an elongated drum 16 shown in greater detail in FIGS. 3 and 4.

Figure 3:
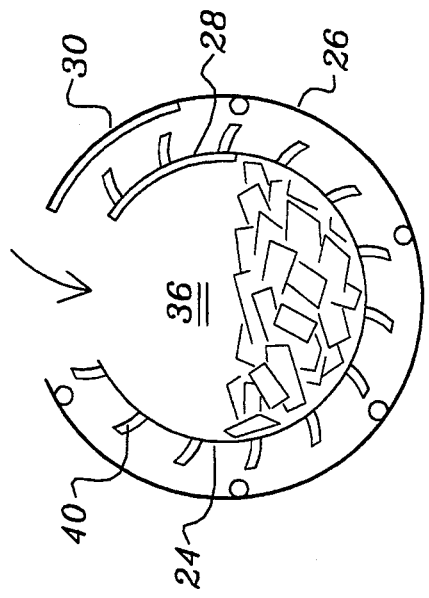
FIG. 3 is an enlarged schematic view of the super-heated steam containing vessel of the inventive system.

In FIG. 3 it may be seen that vessel 16 is axially mounted upon axles 18 and 20 to the interior walls of housing 10 and, through the use of motor 22, may be rotated when it is entirely sealed.

Figure 4A:
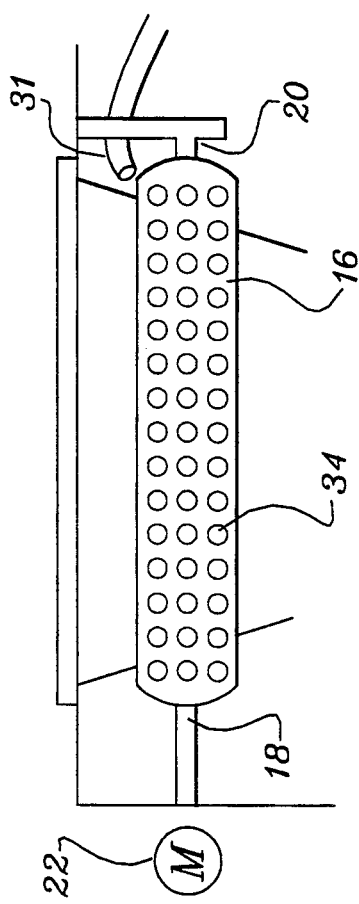
FIGS. 4A thru 4C are a sequence of views showing the loading, operation and dispensing respectively of the super-heated steam containing vessel shown in FIG. 3. Also.
Figure 4C:
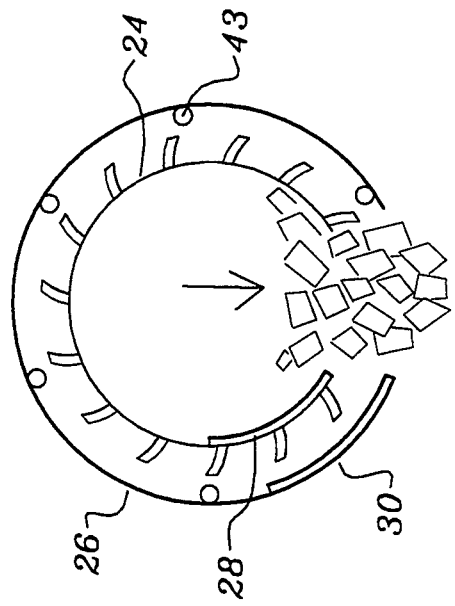
Figure 4B:
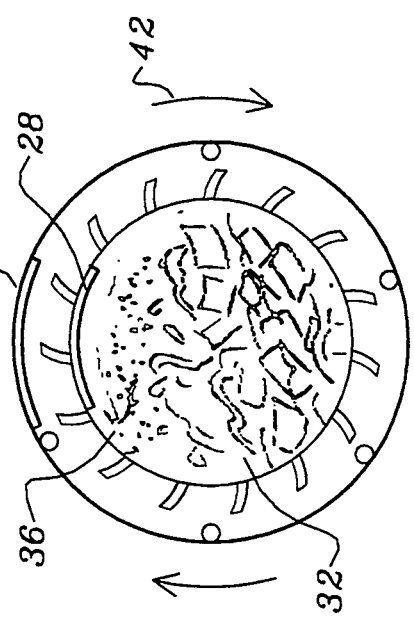

Drum 16 is shown in radial cross-sectional in views FIGS. 4A thru 4C. Therein it may be noted that drum 16 includes of an inner drum 24 and an outer drum 26. Each of said drums are provided with separate longitudinal openings 28 and 30 respectively which openings must be opened to load drum 24 and both of which must be opened to release contents thereof in the manner shown in FIG. 4C. Openings 28 and 30 are closed prior to disinfecting of the contents thereof. This disinfecting occurs after a quantity of water from outlet 31, has filled the lower two or three inches of drum 24, after medical waste 32 has past through openings 28 and 30 of drums 24 and 26. It is noted that inner drum 24 is surrounded by a spiral of resistance heating elements 34. The function of these elements is to heat the surface of inner drum 24 to a temperature in excess of 300 degrees F. such that the interior of inner drum 24 will function in a manner analogous to that of a pressure cooker, that is, the containment of superheated gas which is indicated by dots 36 in FIG. 4B. The superheated gas will completely permeate medical waste 32 such that the heat values within inner drum 24 will extend to every pore and granule of the waste. Also, in the event that there are aerosol-containing capsules within waste 32, such containers will quickly burst within inner drum 24 and the contents thereof will be rapidly disinfected by the pressure and heat of the superheated steam within the inner drum 24.

After a period of about fifteen minutes the resistance heating elements 34 on the surface of inner drum 24 are turned-off. Thereupon the inner and outer drum is rotated per FIG. 4B. It is noted that fins 40 are provided upon the external surface of inner drum 24 such that when the drum is are rotated in the direction indicated by arrow 42 a maximum cooling effect will be imparted to both drums. Holes 43 are provided in outer drum 26 to facilitate escape of heat.

After the temperature within inner drum 24 has fallen below 100 degrees F., the doors 28 and 30 of the respective drums will be oriented downward in the manner shown in FIG. 4C. This will enable the disinfected waste 32 to be dropped downwardly into a matrix 44 of cylindrical grinding elements. The use of a plurality of grinding elements assures that no part of the waste will escape disintegration and, as well, thermal values will be further dispersed during the grinding process. It is to be appreciated that the surfaces of the elements in matrix 44 will possess a variety of configurations such that grinding of maximum efficiency of a broad range of configurations of medical waste will be efficiently accomplished. That is, small grinding surfaces are necessary to grind small items such as hypodermic needles, while larger grinding surfaces are necessary to grind materials having larger dimensions, such as cans or canisters. Accordingly, the top level of grinding element many possess a larger dimension surfaces, the second level somewhat smaller dimension grinding surfaces, and the lowest level of grinding matrix 44 the smallest gauge grinding capability.

Figure 6:
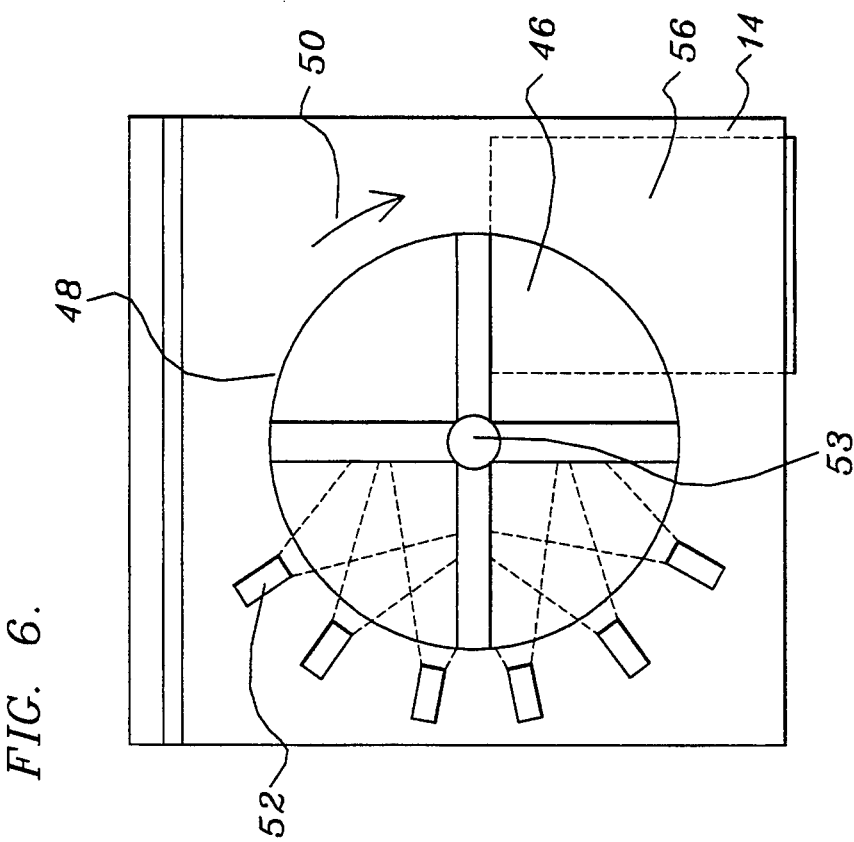
FIG. 6 is a top schematic view of the microwave portion of the system.
Figure 5:
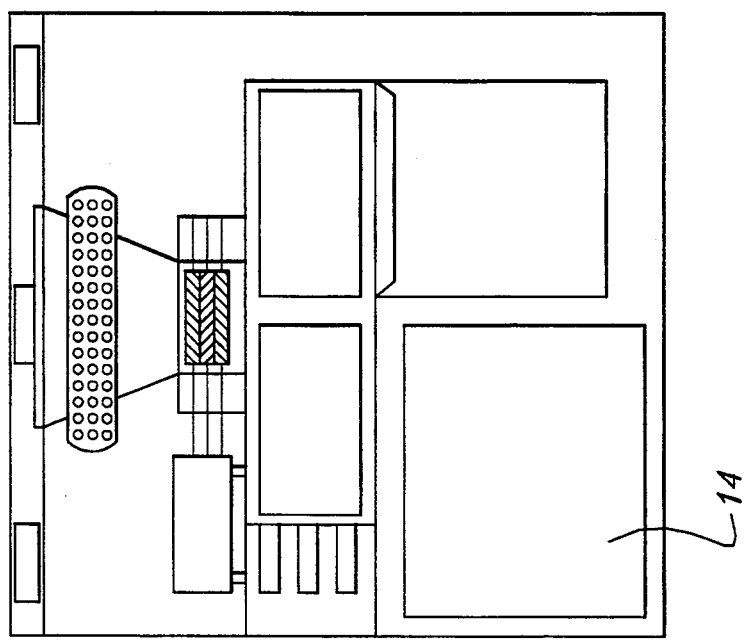
FIG. 5 is a front schematic view of the embodiment of FIG. 1.
Figure 7:
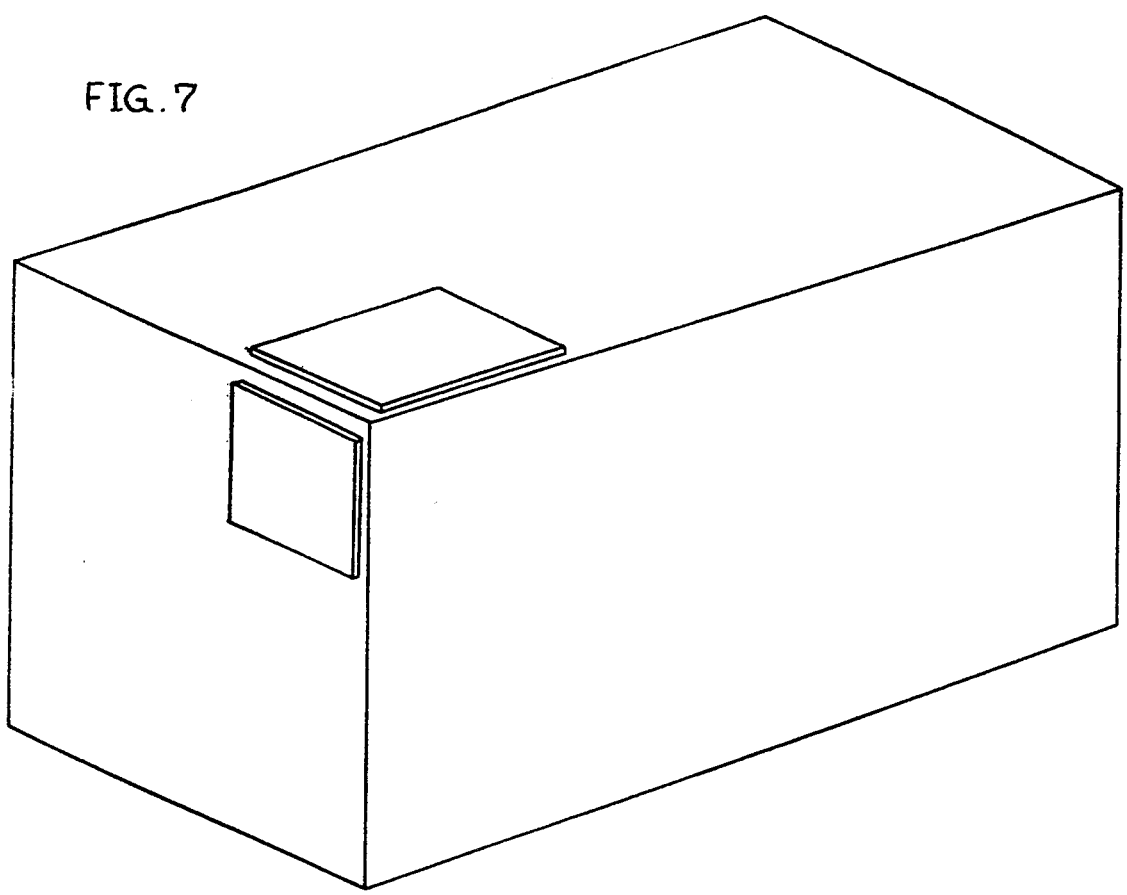
FIG. 7 is a perspective view of a second embodiment of the instant system.
Figure 8:
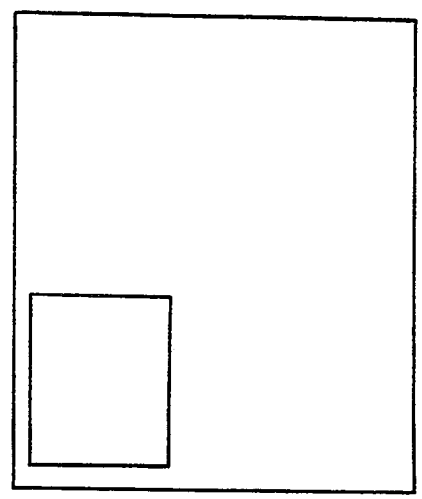
FIG. 8 is a rear plan view of the embodiment of FIG. 7.
Figure 9:
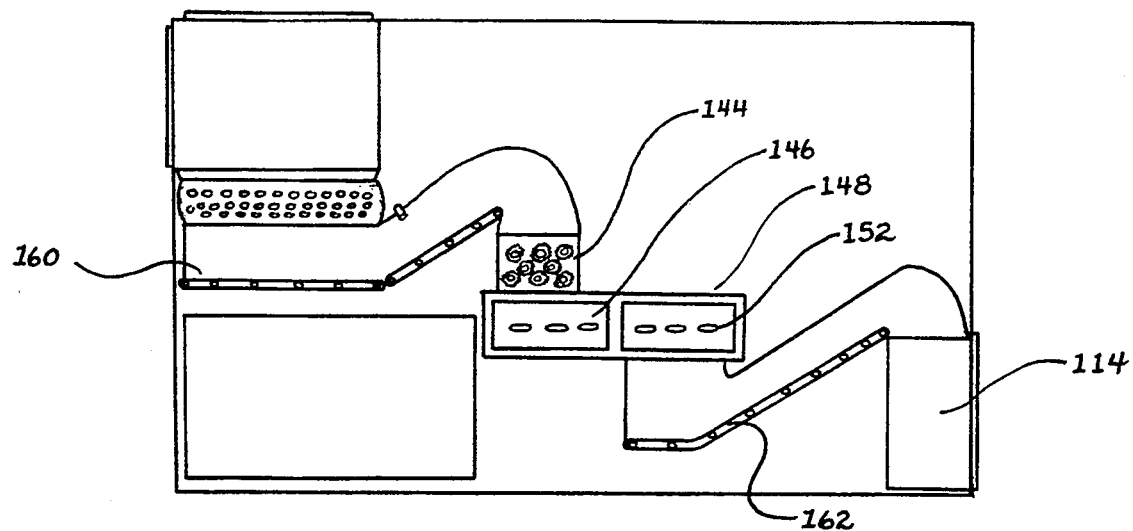
FIG. 9 is a side schematic view of the embodiment of FIG. 7.
Figure 10:
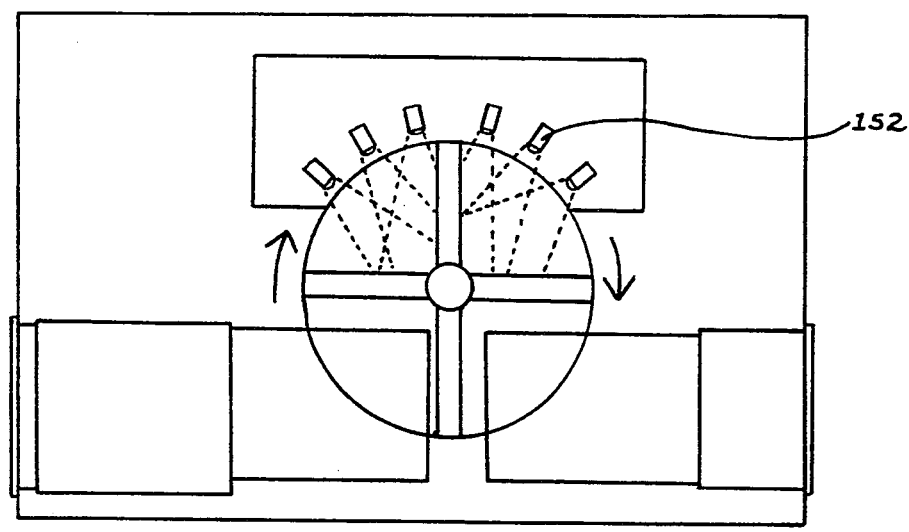
FIG. 10 is a top schematic view of the embodiment of FIG. 7.

Ground medical material is discharged from grinding matrix 44 into compartment 46 of a "lazy susan" type of receiving means 48 which is shown in top view in FIG. 6. Therein it may be noted that the material from compartment 44 is then advanced in direction 50 into exposure to a plurality of microwave elements 52. While each compartment 46 is moving from the position shown at the right of FIG. 6 to the position at the left of FIG. 6, a mist of water that is, water vapor is sprayed thru conduit 53 upon the waste to assure that the microwaving will thoroughly and uniformly penetrate the waste 32. In FIG. 2 there is shown, about microwave elements 52, microwave insulation 54 which assures that radiation will not escape from the housing 10. The Effect of the microwaving is to expose the waste to a temperature of about 275 degrees Fahrenheit for a period of at least thirty minutes. Accordingly, disinfecting occurs both at the beginning and end of the present system such that any pathogens or other infectious material not neutralized at the input step are neutralized at the output step of the system. After microwaving is accomplished the bottom of lazy susan receiving means 48 opens so that the processed waste will drop down chute 56 to output opening 14. It is to be noted that, followed the microwaving step, use may be made of known state of the art compacting and/or encapsulating means (see Background of the Invention) to assure that the medical waste, even after processed, cannot be touched by a medical worker, notwithstanding the fact that after processing in accordance with the present system, there is no necessity to treat the processed waste in any fashion different from that of ordinary residential trash. Therefore, output 14 will typically include a thick gauge plastic bag, e.g., one of five mils such that the output from lazy susan means 46 will be effectively deposited into a bag that a hospital waste disposal worker need do nothing more to than close. It is noted that area 58 (see FIG. 2) is reserved for control electronics of the system.

A second embodiment of the present inventive means is shown in FIGS. 7 thru 10. This system differs from the above described embodiments of FIGS. 1 thru 6 in that it is adapted for larger quantity applications, such as a hospital site, as opposed to within a doctor's office. In this embodiment, the medical waste, after the superheating step involving drums 24 and 26, is dropped onto a conveyor belt 160 and, therefrom, into grinding matrix 144. In the same fashion as in the initially described embodiment, the output of grinding matrix 144 will drop into a first compartment 146 (see FIG. 10) of lazy susan means 148 and, thereafter, will be exposed, at the right side thereof to microwave means 152. It is noted that grinding matrix 144, lazy susan means 148 and microwave assembly 152 differ from that of the first embodiment only in physical dimension. The output of the microwave material is then dropped onto a second conveyor belt means 162 and, therefrom, to output 114. Compaction means will typically be combined with the output area 114 in the system of the embodiment of FIGS. 7 thru 10 in that larger volumes of materials are contemplated.

It is to be appreciated that the second embodiment of the invention described above may be upsized indefinitely as, for example, where off-site medical waste disposal and disinfection are desired.

It has been found that by providing disinfection functions at both the input of all embodiments of the present system, even the most hearty of pathogens will be neutralized. No known pathogens can withstand an operating temperature of more than 270 degrees Fahrenheit which is achieved at both beginning and end of the system.

It is also noted that, at all potential interfaces with the external environment, the embodiments of the instant system are provided with so-called hepa-filters to eliminate any potential, however remote, that may exist for the airborne transmission of pathogens from the system.

It is also noted that the above described system responds to a limitation in prior art microwave approaches to medical waste processing by providing a pathogen neutralizing capability prior to the grinding step such that no mechanical manipulation or disruption of material occurs prior to grinding. Further, in the event that aerosols are contained within particular load of medical waste, there is provided a thick gauge superheating drum 24 such that even the explosion of an aerosol canister would have no effect on the mechanical integrity of the drum 24. No known prior art approach accounts for the possibility of the explosion of an aerosol during the treatment thereof with, thereby, the potential for airborne release of pathogens.

Accordingly, while there has been shown and described the preferred embodiment of the present invention (the embodiment of FIGS. 1 thru 6), it to be appreciated that the invention may be practiced otherwise that is herein specifically shown and described and that, within such embodiment, certain changes may be made in the form and arrangement of the parts without departing from the underlying idea or principles of this invention, within the scope of the Claims appended herewith.

Having thus described my invention what I claim as new, useful and non-obvious and, accordingly, secure by Letters Patent of the United States is:

1. A medical waste disposal system, comprising:
    (a) fluid-tight means for superheating a quantity of untreated medical waste that has been at least partially water saturated to a temperature of at least 275 degrees Fahrenheit for a period of at least thirty minutes, said fluid-tight superheating means having selectably openable and closeable inputs and outputs;
    (b) means for substantially cooling said fluid-tight means after super-heating of said medical waste has been completed;
    (c) a matrix of grinding elements having input surfaces thereof located proximately to said output of said fluid-tight means and having surfaces of respectively different grinding dimensions proportioned to dimensions of medical waste to be processed; and
    (d) means for uniformly exposing to microwave energies ground waste output of said matrix of grinding elements, said exposing means including fluid-misting means directed to said ground waste output prior or during microwaving by said microwave exposing means.

2. The system as recited in claim 1, said system further comprising:
    lazy susan means for receiving an output of said grinding matrix and, thereafter, for furnishing such output into said microwaving exposing means.

3. The system as recited in claim 1, further comprising:
    continuous conveyor belt means for receiving the output of said grinding element matrix and for advancing the same into said microwave exposing means.

4. The system as recited in claim 1, in which said fluid-tight superheating means comprises:
    a vessel surrounded by resistance heating coils which are selectable actuatable to achieve said internal temperature of at least 275 degrees Fahrenheit for at least thirty minutes.

5. The system as recited in claim 4 in which said means for cooling said superheating means comprises:
    means for selectably rotating said fluid-tight means, said means including cooling means formed integrally to the exterior surface of said fluid-tight means.

6. The system as recited in claim 1, further comprising:
    hepafilters provided at all interior-exterior interfaces of said system during the operation thereof.

7. The system as recited in claim 1, further comprising:
    compacting means for processing output of said microwave energy exposing means.

8. The system as recited in claim 1, further comprising encapsulating means for processing output of said microwave energy exposing means.

* * * * *